US012797092B2

(12) United States Patent
Hasenberg et al.

(10) Patent No.: US 12,797,092 B2
(45) Date of Patent: Nov. 17, 2026

(54) LITHOTRIPSY CATHETERS HAVING ELECTRODES FORMED IN METALLIZATION LAYERS

(71) Applicant: Shockwave Medical, Inc., Santa Clara, CA (US)

(72) Inventors: Thomas Charles Hasenberg, Campbell, CA (US); Robert Zelenka, Milpitas, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 0 days.

(21) Appl. No.: 19/387,539

(22) Filed: Nov. 12, 2025

(65) Prior Publication Data

US 2026/0069298 A1 Mar. 12, 2026

Related U.S. Application Data

(63) Continuation of application No. 18/811,481, filed on Aug. 21, 2024, now Pat. No. 12,496,078.
(Continued)

(51) Int. Cl.
*A61B 17/22* (2006.01)
*A61B 17/00* (2006.01)

(52) U.S. Cl.
CPC .. *A61B 17/22022* (2013.01); *A61B 17/00234* (2013.01); *A61B 2017/00238* (2013.01);
(Continued)

(58) Field of Classification Search
CPC ........ A61B 17/22022; A61B 17/00234; A61B 2017/00238; A61B 2017/00292;
(Continued)

(56) References Cited

U.S. PATENT DOCUMENTS 2,916,647 A 12/1959 George
3,412,288 A 11/1968 Ostrander
(Continued)

FOREIGN PATENT DOCUMENTS

AU 2009313507 B2 11/2014
AU 2013284490 B2 5/2018
(Continued)

OTHER PUBLICATIONS

Non-Final Office Action from U.S. Appl. No. 18/811,481, dated Feb. 28, 2025, 11 pages.
(Continued)

*Primary Examiner* — Brooke Labranche
(74) *Attorney, Agent, or Firm* — Paradice & Li LLP

(57) ABSTRACT

A catheter for treating a stenosis in a body lumen includes an elongate tube; a member sealed to a distal end of the elongate tube that is fillable with a conductive fluid; a metallization layer comprising at least one trace forming at least one inner electrode, the metallization layer being connected to at least one wire; and at least one outer electrode extending radially outwardly of the metallization layer and separated from the at least one inner electrode by at least one gap such that, when a voltage pulse is applied to the inner and outer electrodes, current flows across the at least one gap to generate at least one shock wave.

18 Claims, 8 Drawing Sheets

Related U.S. Application Data

(60) Provisional application No. 63/534,426, filed on Aug. 24, 2023.

(52) U.S. Cl.
CPC ............... *A61B 2017/00292* (2013.01); *A61B 2017/00477* (2013.01); *A61B 2017/00526* (2013.01); *A61B 2017/00862* (2013.01); *A61B 2017/00929* (2013.01); *A61B 2017/22025* (2013.01)

(58) Field of Classification Search
CPC .......... A61B 2017/00477; A61B 2017/00526; A61B 2017/00862; A61B 2017/00929; A61B 2017/22025
See application file for complete search history.

(56) References Cited

U.S. PATENT DOCUMENTS

| | | | |
|---|---|---|---|
| 3,413,976 | A | 12/1968 | Roze |
| 3,524,101 | A | 8/1970 | Barbini |
| 3,583,766 | A | 6/1971 | Padberg |
| 3,785,382 | A | 1/1974 | Schmidt-Kloiber et al. |
| 3,902,499 | A | 9/1975 | Shene |
| 3,942,531 | A | 3/1976 | Hoff et al. |
| 4,027,674 | A | 6/1977 | Tessler et al. |
| 4,030,505 | A | 6/1977 | Tessler |
| 4,445,509 | A | 5/1984 | Auth |
| 4,662,126 | A | 5/1987 | Malcolm |
| 4,662,375 | A | 5/1987 | Hepp et al. |
| 4,671,254 | A | 6/1987 | Fair |
| 4,685,458 | A | 8/1987 | Leckrone |
| 4,741,405 | A | 5/1988 | Moeny et al. |
| 4,809,682 | A | 3/1989 | Forssmann et al. |
| 4,813,934 | A | 3/1989 | Engelson et al. |
| 4,878,495 | A | 11/1989 | Grayzei |
| 4,890,603 | A | 1/1990 | Filler |
| 4,900,303 | A | 2/1990 | Lemelson |
| 4,990,134 | A | 2/1991 | Auth |
| 4,994,032 | A | 2/1991 | Sugiyama et al. |
| 5,009,232 | A | 4/1991 | Hassler et al. |
| 5,046,503 | A | 9/1991 | Schneiderman |
| 5,057,103 | A | 10/1991 | Davis |
| 5,057,106 | A | 10/1991 | Kasevich et al. |
| 5,061,240 | A | 10/1991 | Cherian |
| 5,078,717 | A | 1/1992 | Parins et al. |
| 5,102,402 | A | 4/1992 | Dror et al. |
| 5,103,804 | A | 4/1992 | Abele et al. |
| 5,116,227 | A | 5/1992 | Levy |
| 5,152,767 | A | 10/1992 | Sypal et al. |
| 5,152,768 | A | 10/1992 | Bhatta |
| 5,154,722 | A | 10/1992 | Filip et al. |
| 5,176,675 | A | 1/1993 | Watson et al. |
| 5,195,508 | A | 3/1993 | Muller et al. |
| 5,245,988 | A | 9/1993 | Einars et al. |
| 5,246,447 | A | 9/1993 | Rosen et al. |
| 5,254,121 | A | 10/1993 | Manevitz et al. |
| 5,281,231 | A | 1/1994 | Rosen et al. |
| 5,295,958 | A | 3/1994 | Shturman |
| 5,304,134 | A | 4/1994 | Kraus et al. |
| 5,321,715 | A | 6/1994 | Trost |
| 5,324,255 | A | 6/1994 | Passafaro et al. |
| 5,336,234 | A | 8/1994 | Vigil et al. |
| 5,362,309 | A | 11/1994 | Carter |
| 5,364,393 | A | 11/1994 | Auth et al. |
| 5,368,591 | A | 11/1994 | Lennox et al. |
| 5,395,335 | A | 3/1995 | Jang |
| 5,417,208 | A | 5/1995 | Winkler |
| 5,425,735 | A | 6/1995 | Rosen et al. |
| 5,454,809 | A | 10/1995 | Janssen |
| 5,472,406 | A | 12/1995 | de la Torre et al. |
| 5,582,578 | A | 12/1996 | Zhong et al. |
| 5,584,843 | A | 12/1996 | Wulfman et al. |
| 5,603,731 | A | 2/1997 | Whitney |
| 5,609,606 | A | 3/1997 | O'Boyle |
| 5,662,590 | A | 9/1997 | de la Torre et al. |
| 5,709,676 | A | 1/1998 | Alt |
| 5,846,218 | A | 12/1998 | Brisken et al. |
| 5,891,089 | A | 4/1999 | Katz et al. |
| 5,893,840 | A | 4/1999 | Hull et al. |
| 5,931,805 | A | 8/1999 | Brisken |
| 6,007,530 | A | 12/1999 | Dornhofer et al. |
| 6,033,371 | A | 3/2000 | Torre et al. |
| 6,056,722 | A | 5/2000 | Jayaraman |
| 6,080,119 | A | 6/2000 | Schwarze et al. |
| 6,083,232 | A | 7/2000 | Cox |
| 6,090,104 | A | 7/2000 | Webster et al. |
| 6,113,560 | A | 9/2000 | Simnacher |
| 6,132,444 | A | 10/2000 | Shturman et al. |
| 6,146,358 | A | 11/2000 | Rowe |
| 6,186,963 | B1 | 2/2001 | Schwarze et al. |
| 6,210,408 | B1 | 4/2001 | Chandrasekaran et al. |
| 6,215,734 | B1 | 4/2001 | Moeny et al. |
| 6,217,531 | B1 | 4/2001 | Reitmajer |
| 6,267,747 | B1 | 7/2001 | Samson et al. |
| 6,277,138 | B1 | 8/2001 | Levinson et al. |
| 6,287,272 | B1 | 9/2001 | Brisken et al. |
| 6,352,535 | B1 | 3/2002 | Lewis et al. |
| 6,364,894 | B1 | 4/2002 | Healy et al. |
| 6,367,203 | B1 | 4/2002 | Graham et al. |
| 6,371,971 | B1 | 4/2002 | Tsugita et al. |
| 6,398,792 | B1 | 6/2002 | O'Connor |
| 6,406,486 | B1 | 6/2002 | de la Torre et al. |
| 6,440,124 | B1 | 8/2002 | Esch et al. |
| 6,494,890 | B1 | 12/2002 | Shturman et al. |
| 6,514,203 | B2 | 2/2003 | Bukshpan |
| 6,524,251 | B2 | 2/2003 | Rabiner et al. |
| 6,589,253 | B1 | 7/2003 | Cornish et al. |
| 6,607,003 | B1 | 8/2003 | Wilson |
| 6,638,246 | B1 | 10/2003 | Naimark et al. |
| 6,652,547 | B2 | 11/2003 | Rabiner et al. |
| 6,666,834 | B2 | 12/2003 | Restle et al. |
| 6,689,089 | B1 | 2/2004 | Tiedtke et al. |
| 6,736,784 | B1 | 5/2004 | Menne et al. |
| 6,740,081 | B2 | 5/2004 | Hilal |
| 6,755,821 | B1 | 6/2004 | Fry |
| 6,939,320 | B2 | 9/2005 | Lennox |
| 6,989,009 | B2 | 1/2006 | Lafontaine |
| 7,066,904 | B2 | 6/2006 | Rosenthal et al. |
| 7,087,061 | B2 | 8/2006 | Chernenko et al. |
| 7,241,295 | B2 | 7/2007 | Maguire |
| 7,309,324 | B2 | 12/2007 | Hayes et al. |
| 7,389,148 | B1 | 6/2008 | Morgan |
| 7,505,812 | B1 | 3/2009 | Eggers et al. |
| 7,569,032 | B2 | 8/2009 | Naimark et al. |
| 7,850,685 | B2 | 12/2010 | Kunis et al. |
| 7,853,332 | B2 | 12/2010 | Olsen et al. |
| 7,873,404 | B1 | 1/2011 | Patton |
| 7,951,111 | B2 | 5/2011 | Drasler et al. |
| 8,162,859 | B2 | 4/2012 | Schultheiss et al. |
| 8,177,801 | B2 | 5/2012 | Kallok et al. |
| 8,353,923 | B2 | 1/2013 | Shturman |
| 8,556,813 | B2 | 10/2013 | Cioanta et al. |
| 8,574,247 | B2 | 11/2013 | Adams et al. |
| 8,728,091 | B2 | 5/2014 | Hakala et al. |
| 8,747,416 | B2 | 6/2014 | Hakala et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,044,618 | B2 | 6/2015 | Hawkins et al. |
| 9,044,619 | B2 | 6/2015 | Hawkins et al. |
| 9,072,534 | B2 | 7/2015 | Hakala et al. |
| 9,138,249 | B2 | 9/2015 | Adams et al. |
| 9,198,825 | B2 | 12/2015 | Katragadda et al. |
| 9,333,000 | B2 | 5/2016 | Hakala et al. |
| 9,421,025 | B2 | 8/2016 | Hawkins et al. |
| 9,433,428 | B2 | 9/2016 | Hakala et al. |
| 9,522,012 | B2 | 12/2016 | Adams |
| 9,642,673 | B2 | 5/2017 | Adams et al. |
| 9,993,292 | B2 | 6/2018 | Adams et al. |

(56) References Cited

U.S. PATENT DOCUMENTS

| | | | |
|---|---|---|---|
| 10,039,561 | B2 | 8/2018 | Adams et al. |
| 10,118,015 | B2 | 11/2018 | De La Rama et al. |
| 10,149,690 | B2 | 12/2018 | Hawkins et al. |
| 10,154,799 | B2 | 12/2018 | Van Der Weide et al. |
| 10,159,505 | B2 | 12/2018 | Hakala et al. |
| 10,206,698 | B2 | 2/2019 | Hakala et al. |
| 10,517,620 | B2 | 12/2019 | Adams |
| 10,517,621 | B1 | 12/2019 | Adams |
| 10,555,744 | B2 | 2/2020 | Nguyen et al. |
| 10,682,178 | B2 | 6/2020 | Adams et al. |
| 10,702,293 | B2 | 7/2020 | Hawkins et al. |
| 10,709,462 | B2 | 7/2020 | Nguyen et al. |
| 10,828,098 | B2 * | 11/2020 | Gelbart .................. A61B 5/065 |
| 10,959,743 | B2 | 3/2021 | Adams et al. |
| 10,973,538 | B2 | 4/2021 | Hakala et al. |
| 11,000,299 | B2 | 5/2021 | Hawkins et al. |
| 11,076,874 | B2 | 8/2021 | Hakala et al. |
| 11,267,968 | B2 | 3/2022 | Osswald et al. |
| 11,337,713 | B2 | 5/2022 | Nguyen et al. |
| 11,432,834 | B2 | 9/2022 | Adams |
| 11,534,187 | B2 | 12/2022 | Bonutti |
| 11,596,424 | B2 | 3/2023 | Hakala et al. |
| 11,622,780 | B2 | 4/2023 | Nguyen et al. |
| 11,696,799 | B2 | 7/2023 | Adams et al. |
| 11,771,449 | B2 | 10/2023 | Adams et al. |
| 11,911,056 | B2 | 2/2024 | Anderson et al. |
| 12,496,078 | B2 | 12/2025 | Hasenberg et al. |
| 2001/0044596 | A1 | 11/2001 | Jaafar |
| 2002/0045890 | A1 | 4/2002 | Celliers et al. |
| 2002/0082553 | A1 | 6/2002 | Duchamp |
| 2002/0177889 | A1 | 11/2002 | Brisken et al. |
| 2003/0004434 | A1 | 1/2003 | Greco et al. |
| 2003/0176873 | A1 | 9/2003 | Chernenko et al. |
| 2003/0229370 | A1 | 12/2003 | Miller |
| 2004/0006333 | A1 | 1/2004 | Arnold et al. |
| 2004/0010249 | A1 | 1/2004 | Truckai et al. |
| 2004/0044308 | A1 | 3/2004 | Naimark et al. |
| 2004/0097963 | A1 | 5/2004 | Seddon |
| 2004/0097996 | A1 | 5/2004 | Rabiner et al. |
| 2004/0162508 | A1 | 8/2004 | Uebelacker |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0059965 | A1 | 3/2005 | Eberl et al. |
| 2005/0075662 | A1 | 4/2005 | Pedersen et al. |
| 2005/0090888 | A1 | 4/2005 | Hines et al. |
| 2005/0113722 | A1 | 5/2005 | Schultheiss |
| 2005/0113822 | A1 | 5/2005 | Fuimaono et al. |
| 2005/0171527 | A1 | 8/2005 | Bhola |
| 2005/0228372 | A1 | 10/2005 | Truckai et al. |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0069424 | A1 | 3/2006 | Acosta et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2006/0221528 | A1 | 10/2006 | Li et al. |
| 2007/0016112 | A1 | 1/2007 | Schultheiss et al. |
| 2007/0088380 | A1 | 4/2007 | Hirszowicz et al. |
| 2007/0129667 | A1 | 6/2007 | Tiedtke et al. |
| 2007/0156129 | A1 | 7/2007 | Kovalcheck |
| 2007/0239082 | A1 | 10/2007 | Schultheiss et al. |
| 2007/0239253 | A1 | 10/2007 | Jagger et al. |
| 2007/0244423 | A1 | 10/2007 | Zumeris et al. |
| 2007/0250052 | A1 | 10/2007 | Wham |
| 2007/0255270 | A1 | 11/2007 | Carney |
| 2007/0282301 | A1 | 12/2007 | Segalescu et al. |
| 2007/0299481 | A1 | 12/2007 | Syed et al. |
| 2008/0097251 | A1 | 4/2008 | Babaev |
| 2008/0188913 | A1 | 8/2008 | Stone et al. |
| 2009/0041833 | A1 | 2/2009 | Bettinger et al. |
| 2009/0227992 | A1 | 9/2009 | Nir et al. |
| 2009/0230822 | A1 | 9/2009 | Kushculey et al. |
| 2009/0247945 | A1 | 10/2009 | Levit et al. |
| 2009/0254114 | A1 | 10/2009 | Hirszowicz et al. |
| 2009/0299447 | A1 | 12/2009 | Jensen et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0286709 | A1 | 11/2010 | Diamant et al. |
| 2010/0305565 | A1 | 12/2010 | Truckai et al. |
| 2011/0034832 | A1 | 2/2011 | Cioanta et al. |
| 2011/0118634 | A1 | 5/2011 | Golan |
| 2011/0208185 | A1 | 8/2011 | Diamant et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall et al. |
| 2012/0157991 | A1 | 6/2012 | Christian |
| 2012/0203255 | A1 | 8/2012 | Hawkins et al. |
| 2012/0253358 | A1 | 10/2012 | Golan et al. |
| 2013/0030431 | A1 | 1/2013 | Adams |
| 2013/0041355 | A1 | 2/2013 | Heeren et al. |
| 2013/0116714 | A1 | 5/2013 | Adams et al. |
| 2013/0123694 | A1 | 5/2013 | Subramaniyan et al. |
| 2013/0150874 | A1 | 6/2013 | Kassab |
| 2013/0253622 | A1 | 9/2013 | Hooven |
| 2014/0005576 | A1 | 1/2014 | Adams et al. |
| 2014/0046229 | A1 | 2/2014 | Hawkins et al. |
| 2014/0214061 | A1 | 7/2014 | Adams et al. |
| 2015/0320432 | A1 | 11/2015 | Adams |
| 2016/0151081 | A1 | 6/2016 | Adams et al. |
| 2016/0324534 | A1 | 11/2016 | Hawkins et al. |
| 2017/0135709 | A1 | 5/2017 | Nguyen et al. |
| 2017/0311965 | A1 | 11/2017 | Adams |
| 2018/0098779 | A1 | 4/2018 | Betelia et al. |
| 2019/0269426 | A1 * | 9/2019 | Hakala ............. A61B 17/22022 |
| 2021/0085383 | A1 | 3/2021 | Vo et al. |
| 2021/0338258 | A1 | 11/2021 | Hawkins et al. |
| 2022/0015785 | A1 | 1/2022 | Hakala et al. |
| 2022/0240958 | A1 | 8/2022 | Nguyen et al. |
| 2022/0338890 | A1 | 10/2022 | Anderson et al. |
| 2023/0043475 | A1 | 2/2023 | Adams |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |
| 2023/0380849 | A1 | 11/2023 | Adams et al. |
| 2025/0064471 | A1 | 2/2025 | Hasenberg et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 215651484 | U | 1/2022 |
| CN | 120529478 | A | 8/2025 |
| DE | 3038445 | A1 | 5/1982 |
| DE | 202006014285 | U1 | 12/2006 |
| EP | 0442199 | A2 | 8/1991 |
| EP | 0571306 | A1 | 11/1993 |
| EP | 623360 | A1 | 11/1994 |
| EP | 0647435 | A1 | 4/1995 |
| EP | 2253884 | A1 | 11/2010 |
| EP | 2362798 | B1 | 4/2014 |
| EP | 4292553 | A1 | 12/2023 |
| JP | S62-099210 | U | 6/1987 |
| JP | S62-275446 | A | 11/1987 |
| JP | H03-63059 | A | 3/1991 |
| JP | H06-125915 | A | 5/1994 |

(56) References Cited

FOREIGN PATENT DOCUMENTS

| | | | |
|---|---|---|---|
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | 1989011307 | A1 | 11/1989 |
| WO | 1996024297 | A1 | 8/1996 |
| WO | 1999000060 | A1 | 1/1999 |
| WO | 1999002096 | A1 | 1/1999 |
| WO | 2000056237 | A2 | 9/2000 |
| WO | 2004069072 | A2 | 8/2004 |
| WO | 2005099594 | A1 | 10/2005 |
| WO | 2005102199 | A1 | 11/2005 |
| WO | 2006006169 | A2 | 1/2006 |
| WO | 2006127158 | A2 | 11/2006 |
| WO | 2007088546 | A2 | 8/2007 |
| WO | 2007149905 | A2 | 12/2007 |
| WO | 2009121017 | A1 | 10/2009 |
| WO | 2009126544 | A1 | 10/2009 |
| WO | 2009136268 | A1 | 11/2009 |
| WO | 2009152352 | A2 | 12/2009 |
| WO | 2010014515 | A2 | 2/2010 |
| WO | 2010054048 | A2 | 9/2010 |
| WO | 2011006017 | A1 | 1/2011 |
| WO | 2011094111 | A2 | 8/2011 |
| WO | 2011143468 | A2 | 11/2011 |
| WO | 2012025833 | A2 | 3/2012 |
| WO | 2013059735 | A1 | 4/2013 |
| WO | 2014025397 | A1 | 2/2014 |
| WO | 2014025620 | A1 | 2/2014 |
| WO | 2015017499 | A1 | 2/2015 |
| WO | 2019099218 | A1 | 5/2019 |
| WO | 2023169537 | A1 | 9/2023 |

OTHER PUBLICATIONS

Final Office Action from U.S. Appl. No. 18/811,481, dated Jun. 11, 2025, 9 pages.

Notice of Allowance from U.S. Appl. No. 18/811,481, dated Sep. 19, 2025, 7 pages.

International Search Report and Written Opinion received for International Patent Application No. PCT/US2024/043442 mailed on Nov. 25, 2024, 11 pages.

Notification, International Preliminary Report on Patentability, from PCT Application No. PCT/US2024/043442, dated Mar. 5, 2026, 7 pages.

* cited by examiner (a)

(b)

(c)

(d)

(e)

LITHOTRIPSY CATHETERS HAVING ELECTRODES FORMED IN METALLIZATION LAYERS

CROSS-REFERENCE TO RELATED APPLICATIONS

This application is a continuation of U.S. patent application Ser. No. 18/811,481, filed Aug. 21, 2024, now U.S. Pat. No. 12,496,078, and entitled "LITHOTRIPSY CATHETERS HAVING ELECTRODES FORMED IN METALLIZATION LAYERS," which claims the benefit of U.S. Provisional Patent Application No. 63/534,426, filed Aug. 24, 2023, and entitled "LITHOTRIPSY CATHETERS HAVING ELECTRODES FORMED IN METALLIZATION LAYERS," the entire contents of which are hereby incorporated by reference herein.

FIELD OF THE DISCLOSURE

The present disclosure relates generally to the field of medical devices and methods, and more specifically to shock wave catheter devices for treating lesions in a body lumen, such as calcified lesions and occlusions in vasculature and kidney stones in the ureter system.

BACKGROUND

Calcified lesions in body lumens can negatively impact patient health. For example, when calcium builds up in the walls of the coronary arteries, the calcification can restrict blood flow to the heart muscle, which can eventually lead to a heart attack. Catheter devices are one type of device that can be used to treat calcified lesions in a body lumen. When treating lesions with a catheter device, it is important to minimize damage to surrounding soft tissues while still breaking up the lesion as much as possible.

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (e.g., using a relatively low pressure of 2-4 atm) so that the balloon expands to contact the lesion but not to a degree that substantively displaces the lesion. Voltage pulses can then be applied across the electrodes of electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can include electrodes disposed within a closed volume other than an angioplasty balloon, such as a cap, balloons of variable compliancy, or other type of enclosure.

Conventional processes to manufacture IVL catheters can require extensive manual labor, which can lead to high manufacturing costs. For example, conventional manual assembly of an electrode assembly of an IVL catheter can include manually attaching electrodes to an elongate body and manually soldering wires to the electrodes. This process may take hours to complete.

SUMMARY

According to various embodiments, a catheter includes at least one electrode formed by at least one trace of a metallization layer. The metallization layer may be part of a flex circuit (alternatively referred to herein as a "flexible circuit") that can be wrapped around an elongate body of the catheter. The metallization layer may be covered by an insulative cover having cutouts such that one or more regions of the trace(s) of the metallization layer are exposed, for example in regions where the cover has been etched off or removed. The exposed regions of the metallization layer can form the "inner" electrode(s) of one or more electrode pairs, with the outer electrode(s) being mounted outwardly of the insulative cover. Alternatively, rather than being formed as part of a flex circuit, the metallization layer may include traces that are manufactured via wafer fabrication, with an outer electrode layer deposited on an insulating layer and the insulating layer deposited on a metallization layer. In such a configuration, regions of the insulating layer can be selectively removed via etching to create a gap between the traces of the metallization layer and the outer electrode layer.

Electrode assemblies formed in a metallization layer that is part of a flex circuit and/or formed via wafer fabrication can improve the manufacturability of electrode assemblies for shock wave catheters by reducing the amount of manual labor necessary to manufacture shock wave catheters and may enable batch manufacturing. Moreover, manufacturing electrode assemblies in this manner may enable improved electrode designs that reduce the overall diameter of the catheter, thereby reducing the crossing profile of the catheter and allowing the catheter to more easily navigate calcified vessels to deliver shock waves to more severely occluded regions of vasculature.

According to various embodiments, a catheter for treating a stenosis in a body lumen includes an elongate tube; a member sealed to a distal end of the elongate tube that is fillable with a conductive fluid; a metallization layer comprising at least one trace forming at least one inner electrode, the metallization layer being connected to at least one wire; and at least one outer electrode extending radially outwardly of the metallization layer and separated from the at least one inner electrode by at least one gap such that, when a voltage pulse is applied to the inner and outer electrodes, current flows across the at least one gap to generate at least one shock wave.

The metallization layer may include a flex circuit that comprises the at least one trace. The metallization layer may include a flexible base layer with the at least one trace located on the flexible base layer, and a cover layer may cover the at least one trace. The at least one trace is plated onto the flexible base layer or may be vapor deposited onto the flexible base layer. The catheter may include at least one conductive band that includes the at least one outer electrode. The cover layer may include at least one cutout and the at least one conductive band may be aligned with the at least one cutout.

The metallization layer may be wrapped around the elongate tube. The metallization layer may be plated directly onto the elongate tube. For example, the metallization layer may be vapor deposited onto the elongate tube.

The catheter may include an insulating layer that is positioned between the metallization layer and the at least one outer electrode.

According to various embodiments, a system for treating a stenosis in a body lumen includes a voltage source and any of the catheters described above.

According to various embodiments, a catheter for treating a stenosis in a body lumen having a flex circuit further includes a flexible base layer including a first leg extending in a longitudinal direction and a second leg circumferentially offset from the first leg. The flexible base layer may include a connecting portion connecting the first leg and the second leg.

The flex circuit of the catheter may include a metallization layer including a first contact pad, a second contact pad, a first electrode pair including a first electrode and a second electrode spaced apart from the first electrode by a first gap, and a second electrode pair including a third electrode and a fourth electrode spaced apart from the third electrode by a second gap. The flex circuit may include an insulation layer disposed over the metallization layer, with the insulation layer including exposed regions to expose at least a part of each of the first, second, third, and fourth electrodes.

There may be a third electrode pair connected in series to the first and second electrode pairs. Optionally, there may be a fourth electrode pair connected in series to the first, second, and third electrode pairs. When a voltage pulse is applied across the first contact pad and the second contact pad, current may flow across each of the first and second gaps to generate at least one shock wave.

In some embodiments, the first and second electrode pairs are aligned with respect to a longitudinal axis. In some embodiments, the first and second electrode pairs are offset from each other, for example, by a longitudinal distance of 0.2 mm to 5 mm.

According to various embodiments, a method for treating a stenosis in a body lumen includes advancing any of the above catheters described above within the body lumen to a position proximate to the stenosis and applying at least one voltage pulse to the at least one trace via the at least one wire such that current flows across the at least one gap to generate the at least one shock wave. The method may include advancing a guidewire within the body lumen to locate the stenosis and advancing the catheter over the guidewire.

According to various embodiments, a method of manufacturing a shock wave catheter includes forming a flex circuit for an electrode assembly, the flex circuit comprising at least one electrode for generating shock waves; wrapping the flex circuit around an elongate tube; and connecting one or more wires to the flex circuit for delivering voltage pulses to the at least one electrode.

The method may include mounting at least one conductive band at least partially around the flex circuit. The method may include sealing a fluid-fillable member to a distal portion of the elongate tube.

Optionally, forming the flex circuit includes forming at least one trace on a surface of a base layer; and forming a cover layer over the at least one trace, wherein connecting the one or more wires to the flex circuit comprises connecting the one or more wires to the at least one trace. The at least one trace may be formed, for example, by at least one of plating and vapor depositing, and the cover layer is formed by selectively etching regions of the cover layer to expose regions of the at least one trace.

BRIEF DESCRIPTION OF THE FIGURES

Illustrative aspects of the present disclosure are described in detail below with reference to the following drawing figures. It is intended that the embodiments and figures disclosed herein are to be considered illustrative rather than restrictive.

DETAILED DESCRIPTION

Figure 1:
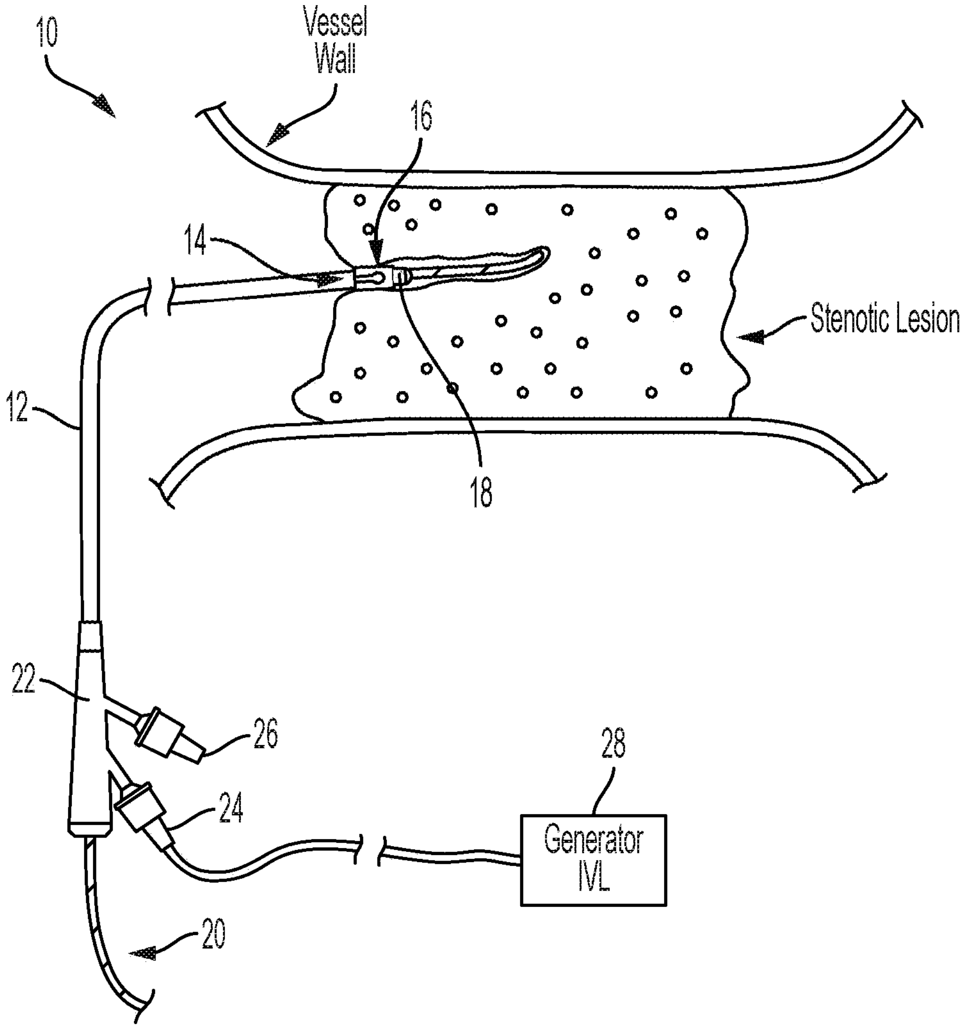
FIG. 1 illustrates an exemplary shock wave catheter being used to treat an occlusion in a blood vessel, according to one or more aspects of the present disclosure.

The following description is presented to enable a person of ordinary skill in the art to make and use the various embodiments disclosed herein. Description of specific devices, assemblies, techniques, and applications are provided only as examples. Various modifications to the examples described herein will be readily apparent to those of ordinary skill in the art, and the general principles described herein will be applied to other examples and applications without departing from the spirit and scope of various embodiments. Thus, the various embodiments are not intended to be limited to the examples described herein and shown, but rather are to be accorded the scope consistent with the claims.

Described herein are catheters incorporating design elements that can improve the manufacturability of an electrode assembly and reduce the overall diameter of the distal end of the catheter, enabling treatment of narrower body lumens and more occluded regions. The catheters can incorporate an electrode assembly that includes a metallization layer having at least one trace that forms at least one electrode. The metallization layer can be formed as a flexible circuit, with a flexible substrate having one or more conductive traces that extend along the substrate. Certain portions of the flexible circuit (such as an insulating cover layer that substantially covers the conductive traces) can be selectively removed to expose the traces of the metallization layer (e.g., for forming an inner electrode). Current can flow from an exposed trace across a gap to an adjacent electrode that may extend radially outwardly of the metallization layer.

The metallization layer can include traces that are formed via a wafer fabrication process. In a wafer fabrication process, an outer electrode layer can be deposited on an insulative layer that is deposited on an inner electrode layer (e.g., the metallization layer) with the traces of the inner electrode layer formed via photomasking and/or etching processes. Manufacturing electrode assemblies according to a wafer fabrication process may enable the creation of complex emitter designs because the photomasking and/or etching processes can realize complex designs accurately. Moreover, the wafer manufacturing process may enable the creation of complex emitter designs that would have been prohibitively expensive to produce using conventional electrode assembly manufacturing processes.

Catheters incorporating a metallization layer as described herein can improve the manufacturability of the electrode assembly of the catheter by reducing the time and cost necessary for manufacturing the inner electrode of the electrode assembly. Further, the metallization layers as described herein can enable catheters with smaller crossing profiles, thereby enabling the catheter to more easily navigate calcified vessels and deliver shock waves to more severely occluded regions of vasculature compared to catheters having larger crossing profiles. Such an electrode assembly design may also facilitate improved and more economical manufacturing of a shock wave catheter by simplifying the process for constructing the electrode assembly.

As used herein, the term “electrode” refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term “electrode pair” refers to two electrodes that are positioned adjacent to each other such that application of a sufficiently high voltage to the electrode pair will cause an electrical current to transmit across the gap (also referred to as a “spark gap”) between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term “emitter” broadly refers to the region of an electrode assembly where the current transmits across the electrode pair, generating a shock wave. The term “emitter sheath” or “emitter band” (which are used interchangeably) refers to a sheath/band of conductive material that may form one or more electrodes of one or more electrode pairs, thereby forming a location of one or more emitters.

Components of emitters, including electrodes and emitter sheaths/bands, may be formed from a metal, such as stainless steel, copper, tungsten, platinum, palladium, molybdenum, cobalt, chromium, iridium, an alloy or alloys thereof, such as cobalt-chromium, platinum-chromium, cobalt-chromium-platinum-palladium-iridium, or platinum-iridium, or a mixture of such materials.

For treatment of an occlusion in a blood vessel, the voltage pulse applied by a power source, including any of the power sources described herein (which may also be referred to herein as voltage sources or pulse generators), is typically in the range of from about five hundred to three thousand volts (500 V-3,000 V). In some implementations, the voltage pulse applied by the voltage source can be up to about ten thousand volts (10,000 V) or higher than ten thousand volts (10,000 V). The pulse width of the applied voltage pulses ranges between two microseconds and six microseconds (2-6 μs). The repetition rate or frequency of the applied voltage pulses may be between about 1 Hz and 10 Hz. The total number of pulses applied by the power source may be, for example, sixty (60) pulses, eighty (80) pulses, one hundred twenty (120) pulses, three hundred (300) pulses, or up to five hundred (500) pulses, or any increments of pulses within this range. Alternatively, or additionally, in some examples, the power source may be configured to deliver a packet of micro-pulses having a sub-frequency between about 100 Hz-10 KHz. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source.

In some embodiments, an IVL catheter is a so-called "rapid exchange-type" ("Rx") catheter provided with an opening portion through which a guide wire is guided (e.g., through a middle portion of a central tube in a longitudinal direction). In other embodiments, an IVL catheter may be an "over-the-wire-type" ("OTW") catheter in which a guide wire lumen is formed throughout the overall length of the catheter, and a guide wire is guided through the proximal end of a hub.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof. As provided herein, it should be appreciated that any disclosure of a numerical range describing dimensions or measurements such as thicknesses, length, weight, time, frequency, temperature, voltage, current, angle, etc. is inclusive of any numerical increment or gradation within the ranges set forth relative to the given dimension or measurement. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

FIG. 1 illustrates an exemplary shock wave catheter 10 being used to treat a lesion in a blood vessel, according to one or more aspects of the present disclosure. The catheter 10 is advanced to a lesion in a patient's vasculature, such as the stenotic lesion depicted in FIG. 1, over a guidewire 20 carried in a guidewire sheath. A distal end 14 of the catheter 10 includes at least one emitter 16 that produces shock waves to break up calcified lesions. In one or more examples, the emitter 16 includes a metallization layer having one or more metal traces that form an inner electrode of an electrode pair, providing a lower profile configuration that reduces the diameter of the distal end 14 of the catheter 10 relative to conventional catheters and permits the treatment of narrower, hard-to-cross lesions.

A flexible cap 18 (e.g., a low-profile flexible angioplasty balloon, a membrane in tension that can flex outward, etc.) is sealably attached to the distal end 14 of the catheter 10, forming an annular channel around the elongate tube 12 of the catheter. The flexible cap 18 surrounds the emitter 16, such that the shock waves are produced in a closed system within the flexible cap 18. The flexible cap 18 is filled with a conductive fluid, such as saline. The conductive fluid allows the acoustic shock waves to propagate outwardly from the electrode pairs of the emitter 16 through the walls of the flexible cap 18 and then into the target lesion. In one or more examples, the conductive fluid may also contain x-ray contrast fluid to permit fluoroscopic viewing of the catheter 10 during use. The flexible cap 18 may be rigid and inflexible.

In some implementations, the material that forms the primary surface(s) of the flexible cap 18 through which shock waves pass can be a noncompliant polymer. In other implementations, a rigid and inflexible structure may be used in lieu of the flexible cap 18. The flexible cap 18 may mitigate thermal injury to soft tissue and reduce cavitation stresses by limiting expansion of the vapor bubbles produced during shock wave generation to the interior of the enclosure. For instance, the vapor bubbles hit the enclosure wall before reaching their maximum potential size, thus inducing collapse, and reducing cavitation stress and preventing soft tissue injury that can be caused by tensile stresses during cavitation bubble collapse.

The catheter 10 includes a proximal end 22 (or handle) that remains outside of a patient's vasculature during treatment. The proximal end 22 includes an entry port for receiving the guidewire 20. The proximal end 22 also includes a fluid port 26 for receiving a conductive fluid for filling and emptying the flexible cap 18 during treatment. An electrical connection port 24 is also located on the proximal end 22 to provide an electrical connection between the distal emitter 16 and a proximal power source 28, such as the intravascular lithotripsy (IVL) generator shown in FIG. 1.

The catheter 10 also includes a flexible elongate tube 12 that extends from the proximal end 22 to the distal end 14 of the catheter. The elongate tube 12 can be formed from a rigid or semi-rigid material, such as a shaped polymeric material. The elongate tube 12 may provide various internal lumens connecting elements of the distal end 14 with the proximal end 22 of the catheter. For example, the elongate tube 12 can include a lumen for receiving the guidewire 20. The elongate tube may include additional lumens extending through the elongate tube 12 or along an outer surface of the elongate tube 12. For example, one or more fluid lumens (e.g., a fluid inlet lumen and a fluid outlet lumen or a combined flush lumen) can be located along or within the elongate tube 12 for carrying conductive fluid from the fluid port 26 into the flexible cap 18. One or more wire lumens may extend along or through the elongate tube 12 for carrying one or more wires that extend from an external voltage source such as the power source 28 to the distal end 14 of the catheter 10.

The power source 28 can supply a series of voltage pulses to the emitters 16. Each voltage pulse initially ionizes the conductive fluid inside the flexible cap 18 to create small gas bubbles around the electrode pair(s) of the emitter 16 that insulates the electrodes. A plasma arc then forms across a gap between the electrodes of the electrode pair(s), creating a low impedance path where current flows freely. The heat from the plasma arc heats the conductive fluid to create a rapidly expanding vapor bubble. The expansion and collapse of the vapor bubble creates a shock wave that radiates outwardly through the annular channel within the flexible cap 18 and then through the blood to the calcified lesion proximate to the flexible cap 18.

Figure 2A:
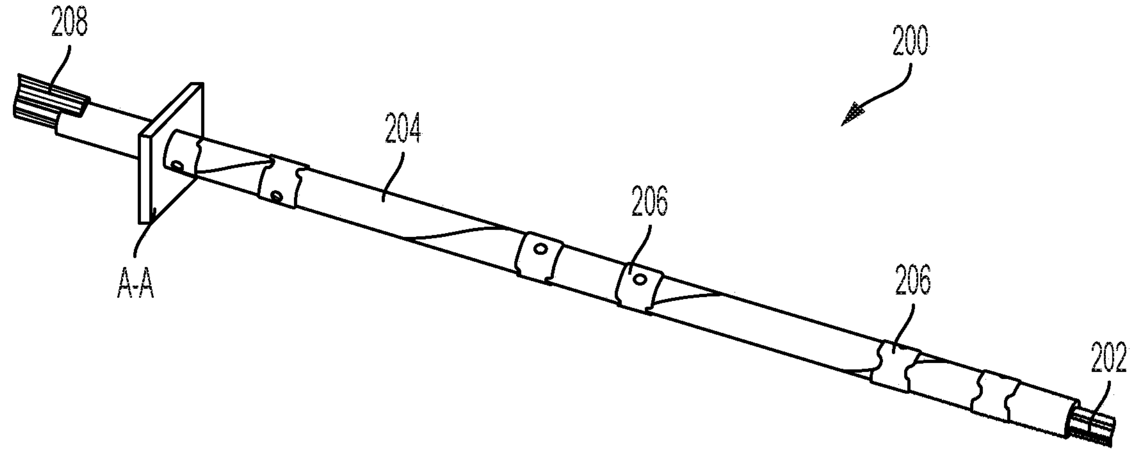
FIG. 2A illustrates a perspective view of an exemplary electrode assembly and FIG. 2B illustrates a cross-sectional view of an emitter of the electrode assembly of FIG. 2A, according to one or more aspects of the present disclosure.

FIG. 2A illustrates a perspective view of an exemplary electrode assembly 200, according to one or more aspects of the present disclosure. The electrode assembly 200 can be included in a catheter, such as the catheter 10 of FIG. 1. In particular, the electrode assembly 200 can be included on a distal end of an elongate tube of a catheter, such as on the distal end 14 of the elongate tube 12 of the catheter 10 of FIG. 1.

The electrode assembly 200 includes a flex circuit 204 having one or more metallic traces (not shown in figure) that form the inner electrodes of a plurality of electrode pairs. The electrode assembly 200 includes one or more emitter bands 206 that form one or more outer electrodes of one or more electrode pairs. The flex circuit 204 can be helically wrapped around an elongate tube 202. The flex circuit 204 may have any suitable number of turns, which may depend on the length of the electrode assembly 200, the number of electrode pair, and/or the distribution of the electrode pairs. The number of turns may be at least one, at least two, at least three, at least four, at least five, at least 10, at least 15, or at least 20. Alternative embodiments of the flex circuit can be otherwise wrapped around an elongate tube, e.g., in an overlapping configuration, with successive electrically joined flex circuits, with a staircase-shaped or rectangularized flex circuit, etc. One or more wires 208 are connected to the flex circuit 204 to provide voltage to the one or more metallic traces of the flex circuit 204.

The emitter bands 206 are conductive bands (e.g., cylindrical, semi-cylindrical, etc.) that are mounted around the flex circuit 204. The emitter bands 206 can be formed from a conductive metal. In one or more examples, the emitter bands 206 may be formed from a refractory metal or metal alloys such as stainless steel, platinum, rhenium, rhodium, palladium, iridium, molybdenum, tungsten, tantalum, copper, or alloys or combinations thereof that has been shaped into an extended tubular or cylindrical shape. The emitter bands 206 can be any desired thickness, for example, between 0.002 and 0.006 inches thick. In various embodiments, the emitter bands 206 have a greater thickness than a thickness of the one or more metallic traces. The emitter bands 206 may be annular, as shown, discontinuous bands (e.g., crescent-shaped), helical, or another suitable shape to mount around the flex circuit 204.

The wires 208 can be insulated wires with insulation extending along the length of the wire (e.g., from a proximal connection to a voltage source to a distal position as part of the electrode assembly 200). The wires 208 may be any suitable shape, such as cylindrical wires or flat wires. Optionally, the wires 208 may include a flattened or crimped portion, such as a crimped distal end.

The wires 208 can be connected to the flex circuit 204 such that the wires 208 provide voltage to the metal traces of the metallization layer. The electrode assembly can include a single pair of wires for driving all of the emitters simultaneously or can include multiple pairs of wires for driving different emitters separately.

Figure 2B:
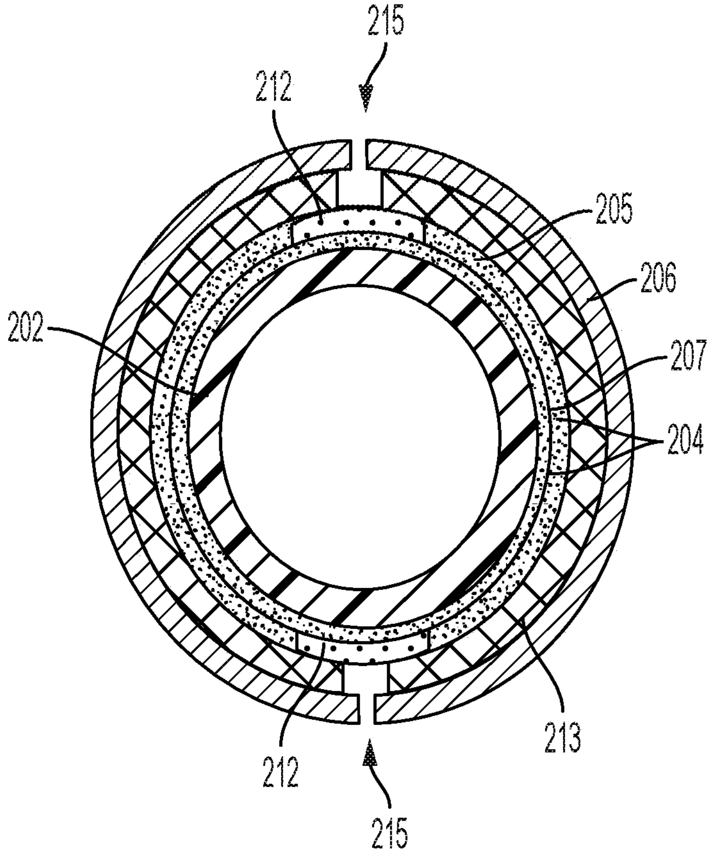

FIG. 2B illustrates a cross-sectional view of electrode assembly 200 at plane A-A of FIG. 2A. This view depicts traces 212 of a metallization layer 205 formed on a flexible base layer 207 of the flex circuit 204 and an insulation layer 213 of the flex circuit 204 that overlays the metallization layer. The flex circuit 204 is wrapped around the elongate tube 202 such that two traces 212 of the metallization layer of the flex circuit 204 are disposed at opposite locations. This illustration is exemplary, as the traces 212 can be positioned and oriented in any desired location and orientation. The emitter band 206 is separated from the metallization layer 205 by the insulation layer 213. The traces 212 and emitter band 206 form two electrode pairs 215, each formed from a respective trace 212 (forming an inner electrode) and a portion of the emitter band 206 (forming an outer electrode). This is provided for example only, as the electrode assembly 200 may include a single electrode pair or more than two electrode pairs at the depicted location. Further, the electrode assembly 200 may include one trace, two traces 212 (as illustrated), three traces, four traces, five traces, or more than five traces, as appropriate for the size and function of the electrode assembly. The traces 212 can be formed from a conductive metal. In one or more examples, the traces can be formed from silver, aluminum, gold, copper, tantalum, tungsten, chromium, titanium, platinum, molybdenum, nickel or any alloy or combination thereof.

In one or more examples, the traces 212 of the flex circuit 204 may be formed via a deposition metallization process. For example, the traces may be formed by vacuum metallizing, wherein a metallic material is heated to its boiling point in a vacuum chamber and then deposited via condensation on a substrate. The traces may be formed via a thermal spray process, wherein metallic material is heated and then sprayed onto a substrate. The traces may be formed via a cold spray process, wherein cold sprayable metallic material is applied to a substrate. When relying on cold spraying, the metallic material may comprise a composite of a metallic powder, a water-based binder, and a hardening agent. The traces may be formed via a hot-dip process, wherein a substrate is dipped into a metallic bath comprising molten metallic material and then removed and allowed to harden.

As shown in FIG. 2B, the electrode pairs 215 are separated from one another by 180 degrees, e.g., circumferentially offset from one another by 180 degrees. In one or more examples, the electrode pairs 215 of an emitter band 206 may be separated from one another by less than 180 degrees. For instance, the electrode pairs 215 of the emitter band 206 can be separated from one another by an angle between 40 degrees and 140 degrees, an angle between 65 degrees and 125 degrees, or an angle between 80 degrees and 100 degrees. As described in U.S. application Ser. No. 17/967,544, which is hereby incorporated by reference, separating electrode pairs that have essentially the same longitudinal location by a circumferential offset of less than 180 degrees can enable the electrode pairs to generate shock waves that constructively interfere to produce a combined shock wave.

The insulation layer 213 may be formed from a non-conductive insulating material that prevents unintended current flow between certain regions of the flex circuit 204 (e.g., portions of the metallic traces) and the emitter band 206. For instance, the insulation layer 213 prevents current from flowing between the trace 212 and the adjacent region of the emitter band 206 of each electrode pair 215. In one or more examples, the insulation layer 213 can be formed from silicon nitride ($SiN_x$), silicon oxide ($SiO_x$), polyimide, polytetrafluoroethylene (PTFE), diamond-like carbon (DLC), thermoplastic polyurethane (TPU), or any combination thereof.

In one or more examples, the flex circuit 204 can include a flexible substrate, such as polyimide, polyether ether ketone (PEEK), or a transparent conductive polyester film, with the traces 212 formed on the surface of the flexible substrate. In such examples, the flex circuit 204 can be a single-sided flex circuit (e.g., a flex circuit having a single conductive layer), a double-sided flex circuit (e.g., a flex circuit having two conductive layers), or a multilayer flex circuit (e.g., a flexible circuit having three or more conductor layers).

Figure 3:
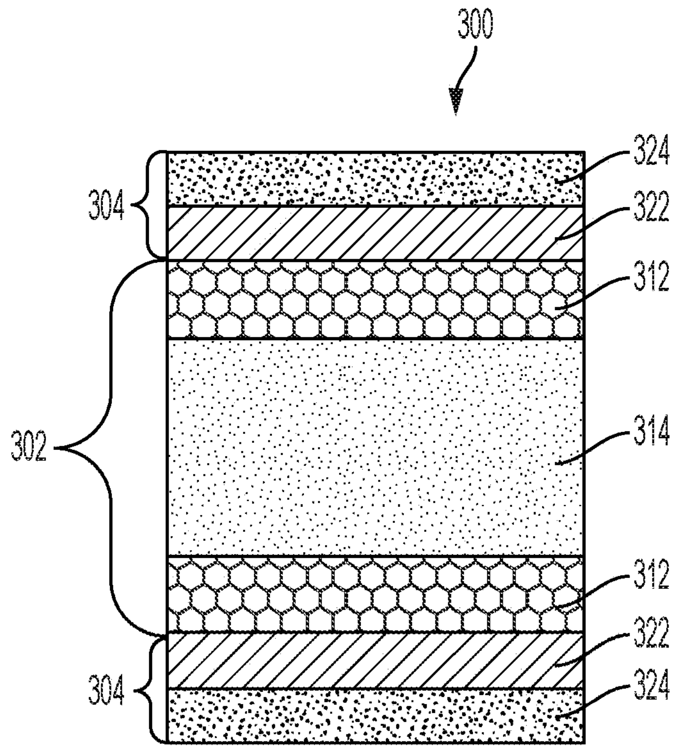
FIG. 3 illustrates a cross-sectional view of an exemplary double-sided flex circuit metallization layer, according to one or more aspects of the present disclosure.

A cross-sectional view of an exemplary double-sided flex circuit 300 is shown in FIG. 3, according to one or more aspects of the present disclosure. The flex circuit 300 can be used in an electrode assembly, such as the electrode assembly 200 of FIG. 2A, and may be used to form inner electrodes in a shock wave catheter, such as the catheter 10 of FIG. 1. In one or more examples, the flex circuit 300 may be manufactured via photolithographic technology and/or by laminating conductive strips between layers of insulation that are coated with an adhesive that is activated during the lamination process.

The flex circuit 300 comprises a layered structure with a metallization layer 302 that is sandwiched between two cover layers 304. The metallization layer 302 includes two layers of conductive layer 312 on either side of an insulative material 314. In one or more examples, the conductive layer 312 is copper and the insulative material 314 is polyimide. The cover layers 304 include a cover material 324 and adhesive 322. In one or more examples, the cover material 324 can include insulative material, such as polyimide. Accordingly, the flex circuit 300 comprises two conductive layers 312 on each side of the insulative material 314, forming the "double-sided" flex circuit structure. The traces of the flex circuit 300 are formed in the conductive layers 312. Portions of one or more of the cover layers 304 can be removed to expose portions of one or more of the conductive layers 312 such that current can flow between the conductive layer 312 and an adjacent conductive material (e.g., between inner and outer electrodes as described above). One or more conductive pathways can be formed between the conductive layers (e.g., vias extending through insulative material 314) to interconnect one or more traces of the conductive layers 312.

In one or more examples, the total thickness of the flex circuit 300 can be less than 150 μm. For instance, the cover material 324 and the adhesive 322 can be about 12 μm thick, the conductive layers 312 can be about 18 μm thick, and the insulative material 314 can be about 50 μm thick.

Figure 4:
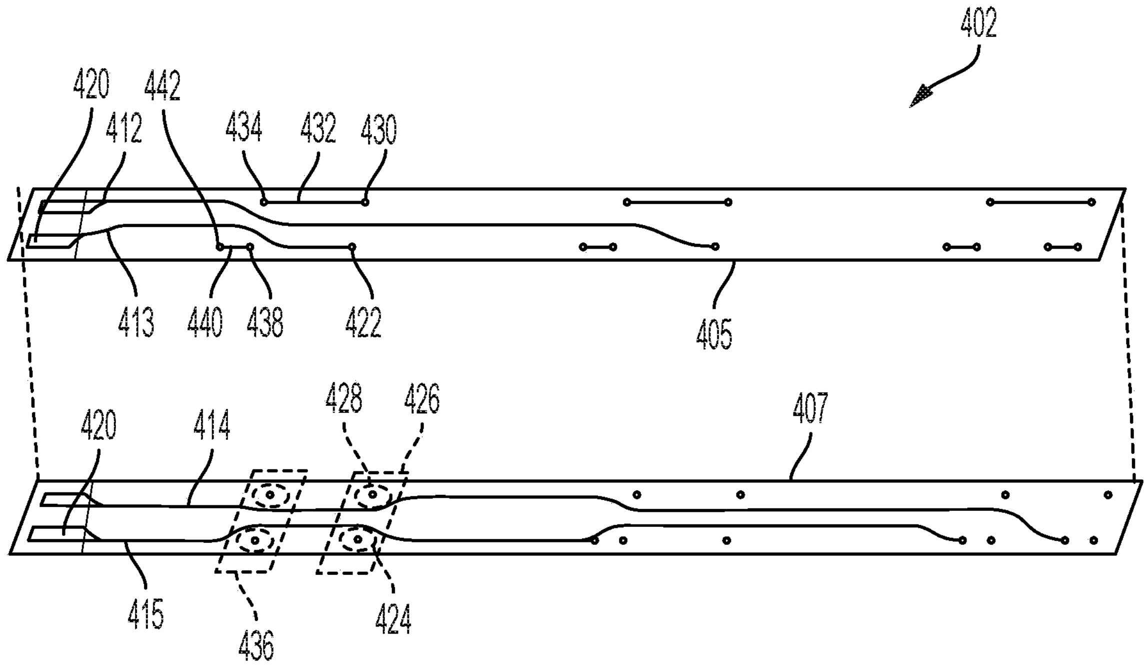
FIG. 4 illustrates an exploded perspective view of conductive traces of a metallization layer, according to one or more aspects of the present disclosure.

An exploded perspective view of conductive traces of an exemplary flex circuit 402 that includes two layers of conductive traces is shown in FIG. 4, according to one or more aspects of the present disclosure. The flex circuit 402 is shown in its pre-wrapped state before being wrapped around an elongate tube, such as tube 202 of FIG. 2A. The flex circuit 402 includes a first conductive layer 405 and a second conductive layer 407, which may be separated from one another by an insulative layer when assembled, similarly to the flex circuit 300 of FIG. 3. In addition, a cover layer can be located on an outer surface of the first conductive layer 405 and/or the second conductive layer 407, similarly to the flex circuit 300 of FIG. 3. The flex circuit 402 can be used in an electrode assembly, such as the electrode assembly 200 of FIG. 2A, and may be used to form electrodes for a shock wave catheter, such as the catheter 10 of FIG. 1.

Each of the first conductive layer 405 and the second conductive layer 407 include at least one trace. In particular, the first conductive layer 405 includes a first trace 412 and a second trace 413 and the second conductive layer 407 includes a third trace 414 and a fourth trace 415. Each of the first conductive layer 405 and the second conductive layer 407 can be formed from metal traces disposed on a flexible substrate material, such as a flexible polymer film (e.g., polyester (PET), polyimide (PI), polyethylene naphthalate (PEN), polyetherimide (PEI), fluoropolymers (FEP), copolymers, and any combination thereof). The traces 412, 413, 414, and 415 can be formed from any suitable conductive material. For example, the traces may be formed from a metallic foil such as a copper foil, which may be electrodeposited or wrought. In one or more examples, the traces may be plated onto the flexible substrate or vapor deposited onto the flexible substrate. Suitable methods of vapor deposition can include sputtering deposition, arc vapor deposition, atomic layer deposition, thermal evaporation deposition, and any other suitable vapor deposition methods. In some embodiments, metallic traces are formed by a physical vapor deposition process. In some embodiments, metallic traces are formed by a chemical vapor deposition process.

Each of the traces includes a metal pad 420 for connecting the trace to a respective wire for connecting the trace to the external power source. In the illustrated example, the four traces 412, 413, 414, and 415 can be connected to four wires to form three circuits in which trace 415 serves as the ground pathway for the three circuits. Taking trace 413 as an example, when a voltage is applied across the pads 420 of trace 413 and trace 415, current travels from pad 420 of trace 413, through trace 413 to a via 422 located at the distal end of trace 413 (for simplicity, only the end portions of the via that lie within the conductive layers 405, 407 are shown). The via 422 extends to the conductive layer 407 and forms an inner electrode of a first electrode pair. The outer electrode of the first electrode pair may be formed by a hole 424 in a first emitter band 426 (shown by a rectangular shape for convenience). The current can travel as a spark from the via 422 to the emitter band 426 (thus creating one or more shockwaves at that location) and then through the emitter band 426 to a second hole 428 that provides an outer electrode of a second electrode pair. The inner electrode of the second electrode pair is provided by a via 430, which leads to a distal end of a trace 432. Current travels as a spark from the first emitter band 426 (at hole 428) to the via 430 (thus creating one or more shockwaves at that location). Current then travels through trace 432 to via 434, which forms an inner electrode of an electrode pair in which the outer electrode is provided by a second emitter band 436. Current travels as a spark from via 434 to the second emitter band 436, through the second emitter band 436, and as a spark from the second emitter band 436 to via 438. Current then travels through trace 440 (which is connected at one end to via 434) to via 442, which extends from layer 405 to layer 407 where it connects with trace 415. Thus, application of voltage to trace 413 and trace 415 can create shockwaves at four locations. Similar current flow is provided by traces 412 and 414.

Figure 5A:
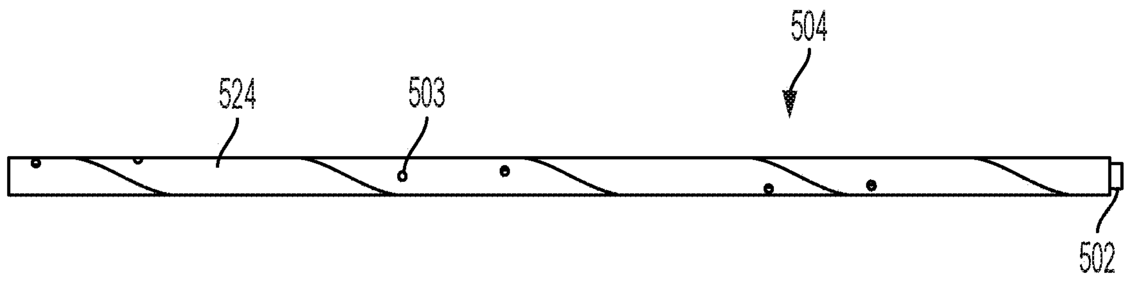
FIG. 5A depicts an exemplary metallization layer mounted to an elongate tube, according to one or more aspects of the present disclosure.

As noted above, certain portions of a flex circuit can be removed to expose the traces of a metallization layer such that current can flow between the traces and an adjacent conductive material, such as the emitter bands 206 of FIG. 2A. FIG. 5A depicts an exemplary flex circuit 504 mounted to an elongate tube 502, according to one or more aspects of the present disclosure. The flex circuit 504 can be configured as the flex circuit 300 of FIG. 3, with one or more conductive layers that are covered by a cover material. The traces of the flex circuit 504 are thus not visible in FIG. 5A, because the outermost portion of the flex circuit 504 is a cover material 524. To provide a location for current to flow freely from the traces of the flex circuit 504 and outer electrodes such as emitters, the flex circuit 504 includes cutouts 503.

Figure 5B:
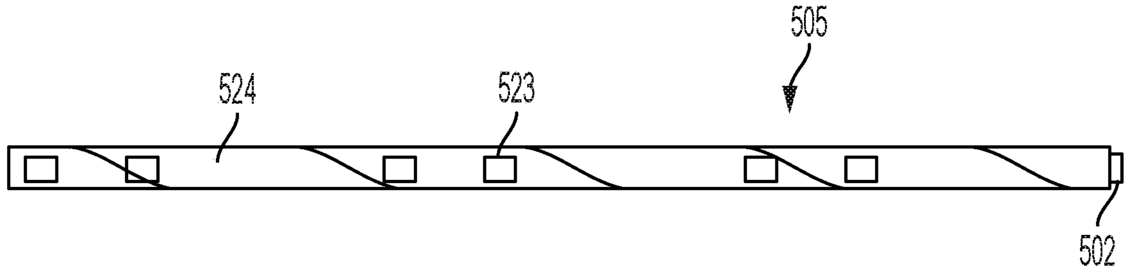
FIG. 5B depicts an exemplary metallization layer mounted to an elongate tube, according to one or more aspects of the present disclosure.

As shown in FIG. 5A, the cutouts 503 can be circular cutouts, which can be aligned with outer electrodes (e.g., of one or more electrode bands) to create electrode pairs. For instance, returning to FIG. 2A, the emitter bands 206 can be aligned with circular cutouts of the flex circuit 204 to create electrode pairs that can generate shock waves. However, the cutouts 503 may be any suitable shape (e.g., elliptical, triangular, quadrilateral, etc.). For instance, FIG. 5B depicts an exemplary flex circuit 505 mounted to an elongate tube 502, according to one or more aspects of the present disclosure, in which the flex circuit 505 has square-shaped cutouts 523. The square-shaped cutouts can similarly be aligned with outer electrodes such as provided by the emitter bands 206 of FIG. 2A to create electrode pairs. Other suitable cutout shapes may be, for example, slots that extend circumferentially and/or longitudinally along the metallization layer when it is mounted to the elongate tube. The cutouts may be formed via any suitable removal process such as an etching process, laser cutting, waterjet cutting, mechanical cutting, etc.

A flex circuit can be incorporated into a shock wave catheter in a number of ways. For example, the metallization layer may be mounted to an elongate tube of a catheter by being wrapped around the elongate tube and secured via an adhesive. For example, the flex circuit 504 and flex circuit 505 of FIGS. 5A and 5B are strips that are helically wrapped around the elongate tube 502. Alternatively, wafer manufacturing processes may be used to directly form a metallization layer on an elongate tube of the catheter. For example, a metallization layer (including multiple conductive layers separated by one or more insulated layers as described with respect to FIG. 3) may be plated or vapor deposited directly onto the elongate tube.

Figure 6A:
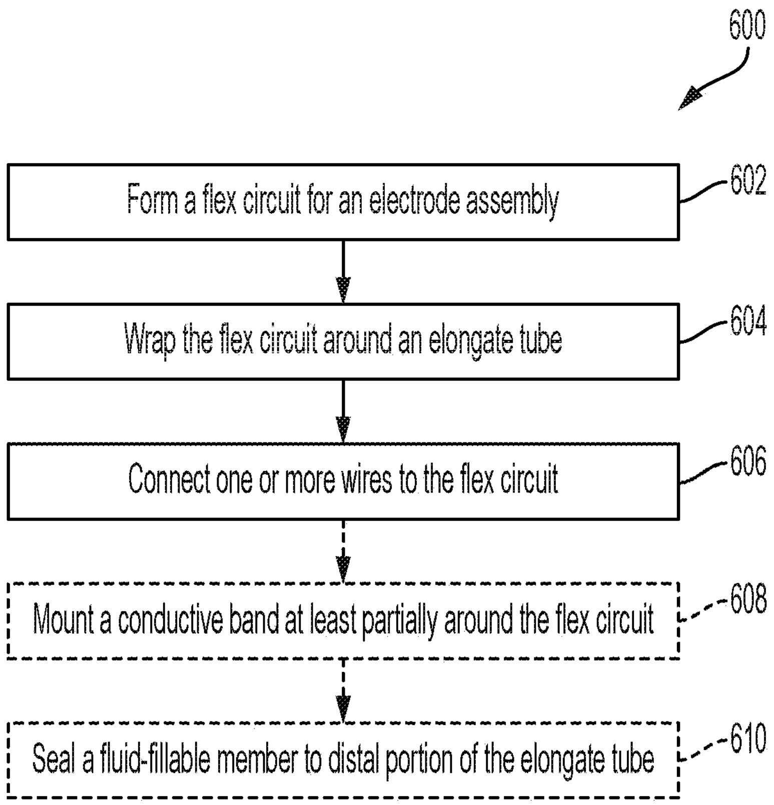
FIG. 6A is a block diagram of an exemplary method of manufacturing a shock wave catheter.
Figure 6B:
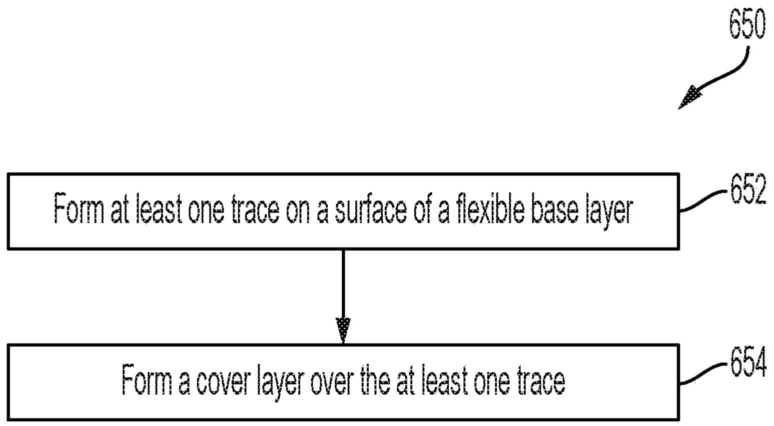
FIG. 6B is a block diagram of an exemplary wafer manufacturing process for forming a flex circuit, according to one or more aspects of the present disclosure.

FIG. 6A is a block diagram of an exemplary method 600 of manufacturing a shock wave catheter, such as shock wave catheter 10 of FIG. 1, with a flex circuit. At step 602, a flex circuit for an electrode assembly is formed. In one or more examples, a flex circuit for incorporation into a shock wave catheter can be formed via a wafer manufacturing process. A block diagram of an exemplary wafer manufacturing process 650 is shown in FIG. 6B and graphically illustrated in FIG. 7, according to one or more aspects of the present disclosure. At step 652, at least one trace is formed on a surface of a base layer. For example, as depicted in step (a) of FIG. 7, a wafer manufacturing process can begin with depositing a conductive layer 711 on a substrate 720. Optionally, substrate 720 can be a flexible substrate. It should be noted that rather than depositing such material on a substrate, the material may be deposited directly on an elongate tube of a catheter. As above, the conductive layer 711 can be, for example silver, aluminum, gold, copper, tantalum, tungsten, chromium, titanium, platinum, molybdenum, or any alloy or combination thereof. The conductive layer can be formed in any suitable manner, including by plating or vapor depositing. A pattern with photoresist can be photo-masked onto the surface of the conductive layer 711. The photoresist can be positive photoresist that breaks down when exposed to ultraviolet light, leaving exposed areas unprotected, or negative photoresist that hardens when exposed to ultraviolet light, leaving unexposed areas unprotected. Thus, after exposing the photoresist-coated material to ultraviolet light and subsequently processing to uncover unprotected areas in the conductive layer 711, these unprotected areas of the conductive layer 711 can be removed by an etching process, as shown in step (b) of FIG. 7, which results with two adjacent strips of conductive material, forming conductive traces 712.

At step 654, a cover layer is formed over at least one trace. For example, as shown in step (c) of FIG. 7, the traces 712 can then be coated with an insulative layer 714. As above, the insulative material can be, for example, $SiN_x$, $SiO_x$, polyimide, PTFE, DLC, or any combination thereof. Thereafter, the insulative layer 714 can be coated with a second conductive layer 706, which may be formed from the same material as the conductive layer 711 forming the traces 712, or by another conductive material.

Once the second conductive layer 706 is applied, the substrate 720 can be removed and the multi-layered structure 716 can be formed into individual emitters or groups of individual emitters. For instance, the multi-layered structure 716 may be cut into individual emitters (or groups of emitters) each having at least one pair of electrodes (a trace 712 separated from a portion of the second conductive layer 706 by a strip of insulative layer 714). Wires can then be attached to these individual emitters to generate shock waves when voltage is applied to an electrode of each electrode pair as described above. In some variations, the substrate 720 is not removed.

Figure 7:
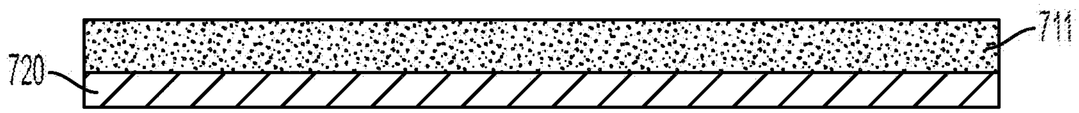
FIG. 7 graphically depicts an exemplary wafer manufacturing process, according to one or more aspects of the present disclosure.
Figure 7:
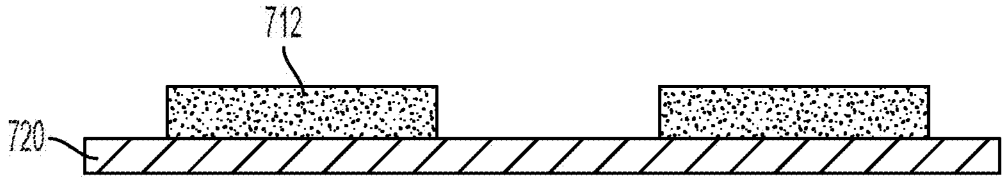
Figure 7:
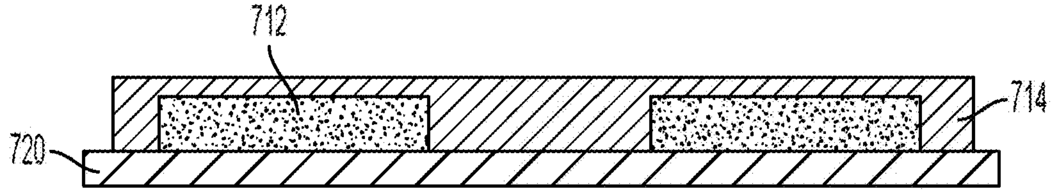
Figure 7:
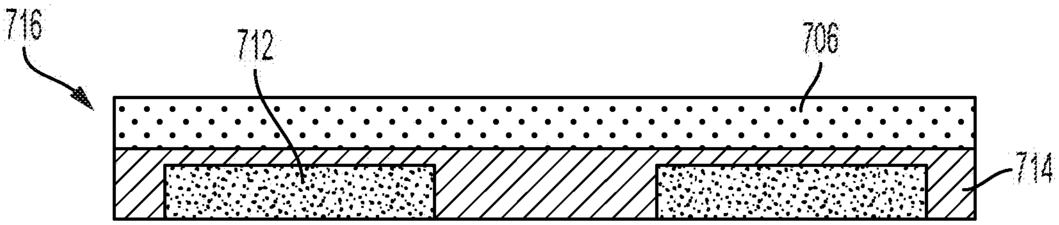
Figure 7:
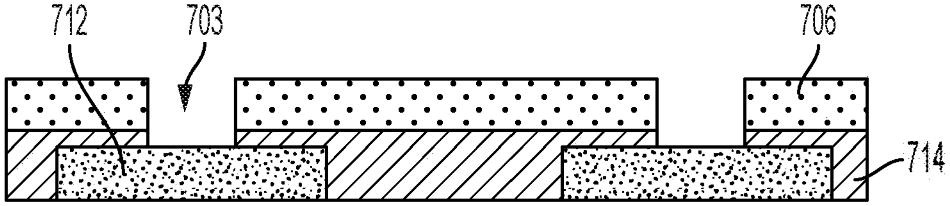

As shown in the configuration depicted in step (d) of FIG. 7, there is no cutout in the insulative layer 714 between the traces 712 and the second conductive layer 706. In such configuration, the current path can be from the exposed faces of the traces 712 and the second conductive layer 706. Alternatively, a cutout 703 can be made in the second conductive layer 706 and insulative layer 714 (e.g., by selectively etching regions of the cover layer to expose regions of the traces 712) that defines a central current path, as shown in step (e) of FIG. 7. In particular, the cutout 703 forms a path for current to flow between the trace 712 and the second conductive layer 706 via the insulation-removed cutout 703.

Returning to FIG. 6A, at step 604, the flex circuit can be wrapped around an elongate tube. For example, as described above with respect to FIG. 2A, flex circuit 204 can be helically wrapped around an elongate tube 202. At step 606, one or more wires can be connected to the flex circuit. For example, with respect to FIG. 4, wires can be connected to metal pads 420 after the flex circuit 402 has been wrapped around an elongate tube.

In some variations, method 600 can include step 608 in which one or more conductive bands, such as emitter bands 206 of FIG. 2A and FIG. 2B, are mounted at least partially around the flex circuit. Optionally, at step 610, a fluid fillable member, such as flexible cap 18, can be sealed to a distal portion of the elongate tube, surrounding the electrodes of the flex circuit.

Manufacturing electrode assemblies according to a wafer manufacturing process as shown in FIG. 7 may enable the creation of complex emitter designs because the photomasking and/or etching processes can realize complex designs accurately. Moreover, the wafer manufacturing process may enable the creation of complex emitter designs that would have been prohibitively expensive to produce using previous manufacturing processes. Additionally, the wafer manufacturing process may enable shock wave catheters having lower crossing profiles by eliminating the need for a separate emitter band and any dielectric layer associated with the emitter band, thus reducing the diameter of the catheter by at least twice the radial thickness of the emitter band and the dielectric layer.

When a metallization layer is incorporated into a shock wave catheter such as the catheter 10 of FIG. 1, the metallization layer can be mounted to (or deposited on) an elongate tube, with portions of the metallization layer acting as the "inner" electrodes of an electrode assembly. For instance, returning to FIG. 5A, the cutouts 503 of the metallization layer of the flex circuit 504 act as the "inner" electrodes of an electrode assembly, and the "outer" electrodes can be formed from, for example, the emitter bands 206 of FIG. 2A.

Figure 8A:
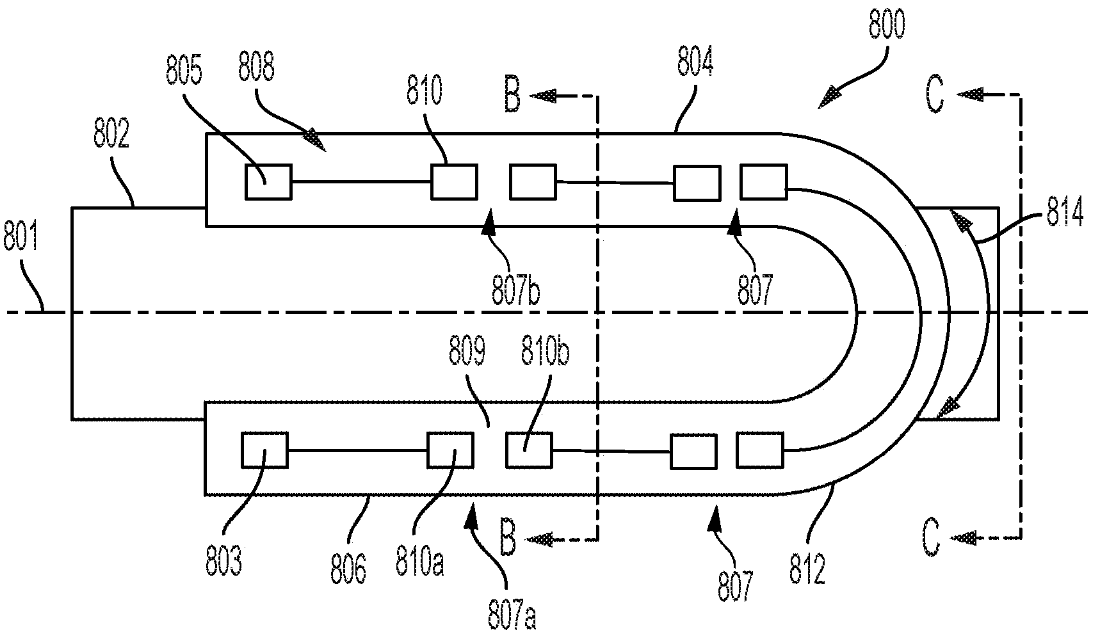
FIGS. 8A-C illustrate an example of mounting a flex circuit to an elongate member in which the flex circuit is wrapped only partially around the elongate member, according to one or more aspects of the present disclosure.
Figure 8B:
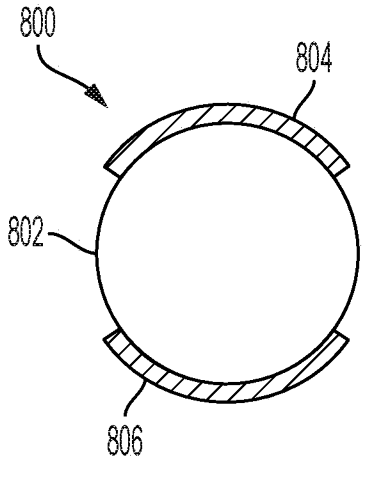
Figure 8C:
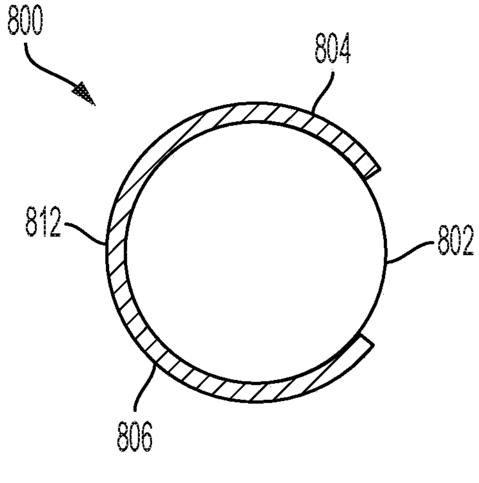

FIGS. 8A-C illustrate an example of mounting a flex circuit to an elongate member in which the flex circuit is wrapped only partially around the elongate member. FIG. 8A illustrates a flex circuit 800 in a pre-mounted state in which the flex circuit 800 is generally planar. Also shown is a side view of an elongate member 802 to which the flex circuit 800 is to be mounted. The flex circuit 800 includes a first leg 804 that will mount to an upper portion of the elongate member 802 with respect to the view of FIG. 8A and a second leg 806 that will mount to a lower portion of the elongate member with respect to the view of FIG. 8A. Each leg 804, 806 includes at least one trace 808 that includes at least one electrode 810. The legs 804, 806 are connected by a connecting portion 812 that wraps at least partially around the elongate member 802 in direction 814 when mounted. When mounted, the first and second legs 804, 806 can extend longitudinally along the elongate member 802, with the second leg 806 being circumferentially offset from the first leg 804 with respect to a longitudinal axis 801 of the elongate member 802.

FIGS. 8B and 8C are views along planes B-B and C-C, respectively of FIG. 8A with the flex circuit 800 mounted to the elongate member 802. Looking first at FIG. 8B, which is a cross-section midway along the flex circuit 800, the first leg 804 extends along the upper portion of the elongate member 802 and the second leg 806 extends along the lower portion of the elongate member 802. Looking at the distal end of the elongate member 802, as shown in FIG. 8C, the connecting portion 812 extends along the elongate member 802, connecting the first and second legs 804, 806. The illustrated example shows the elongate member 802 as having a cylindrical shape. However, the elongate member can be any suitable shape. In some variations, the elongate member has flats formed where the first and second legs 804, 806 are disposed so that the first and second legs 804, 806 can lay flat, without curvature.

The flex circuit 800 includes shock wave emitters 807, each formed by a pair of electrodes spaced apart by a gap. For example, flex circuit 800 may include shock wave emitter 807*a* formed by an electrode pair that includes a first electrode 810*a* and a second electrode 810*b* spaced apart by a gap 809. Before the flex circuit 800 is mounted to the elongate member 802, the first and second electrodes may be coplanar. FIG. 8A depicts four shock wave emitters 807 connected in series, but more or fewer shock wave emitters (e.g. 2 emitter, 3 emitters, 5 emitters, 8 emitters, 10 emitters, etc.) may be connected in series or may be grouped into multiple channels. The flex circuit 800 may be connected at a first pad 803 and a second pad 805 to conductive members connected to a first and second terminal of a pulse generator. When a voltage pulse is applied across the first and second contact pads via the first and second terminals, a shock wave may be generated and emitted at each gap between the electrodes of the electrode pairs of the shock wave emitters 807 of the flex circuit 800 due to the flow of current across the gaps between electrodes 810.

As shown and described with respect to other examples (e.g. FIGS. 2A and 2B), flex circuit 800 may include a flexible base layer on which the first leg and the second leg are disposed. The first and second contact pads and electrode pairs can be part of a metallization layer. Optionally, an insulation layer can be disposed over the metallization layer, and the insulation layer may include exposed regions that expose one or more of the electrode pairs underneath. The exposed regions of the insulation layer may expose at least a part of one or both electrodes making up any of the electrode pairs.

In some embodiments, a shock wave emitter 807 located on the first leg 804 and a shock wave emitter 807 located on the second leg 806 may be aligned with respect to the longitudinal axis 801 (i.e., in the same longitudinal position). For example, in FIG. 8A, shock wave emitter 807*a* is aligned with shock wave emitter 807*b* with respect to the longitudinal axis 801. Aligning the shock wave emitters 807 with respect to the longitudinal axis 801 may provide a region of high sonic output where the shock wave emitters 807 are aligned. In some embodiments, the first and second legs may include shock wave emitters 807 that are offset with respect to the longitudinal axis 801 (i.e., at different longitudinal positions) so as to provide a more uniform sonic output along the length of the shock wave emitting region of the catheter. In some embodiments, shock wave emitters may be offset from each other by a longitudinal distance of 0.2-5 mm, 1-5 mm, or 1-10 mm. In some embodiments, shock wave emitters may be offset from each other by a longitudinal distance of less than or equal to 0.2 mm, 0.5 mm, 1 mm, 1.5 mm, 2 mm, 2.5 mm, 3 mm, 3.5 mm, 4.0 mm, 4.5 mm, 5 mm, or 10 mm. In some embodiments, shock wave emitters may be offset from each other by a longitudinal distance of greater than or equal to 0.1 mm, 0.2 mm, 0.5 mm, 1 mm, 1.5 mm, 2 mm, 2.5 mm, 3 mm, 3.5 mm, 4 mm, 4.5 mm, or 5 mm.

Flex circuit 800 may be adhered to the elongate member 802 by a glue or an epoxy. In some embodiments, instead of a flexible base layer, the metallization layer may be formed directly on the elongate member 802. In some embodiments, an outer tubing (e.g., a heat-shrink tubing) with cutouts to expose the electrode surfaces may be used to immobilize the flex circuit 800.

Further, although flex circuit 800 is illustrated as having two legs in a U-shape in FIG. 8A, flex circuit 800 may have more than two legs in embodiments having larger profile elongate members. For example, flex circuit 800 may have three legs arranged in an S-shape. In this case, one or more shock wave emitters on a first leg may be approximately 120 degrees offset from one or more shock wave emitters on a second leg, and the one or more shock wave emitters on the second leg may be approximately 120 degrees offset from the shock wave emitters on the third leg. In another example, flex circuit 800 may have four legs with shock wave emitters on each leg being approximately 90 degrees offset from one or more shock wave emitters on the next leg.

In addition to the above benefit of reducing the crossing profile of a shock wave catheter, incorporating a metallization layer to form the inner electrodes of the electrode assembly of the catheter can improve the manufacturability of the shock wave catheter. For instance, previous electrode assemblies can rely on a touch-intensive manufacturing process with electrode assemblies being assembled by hand. In contrast, manufacturing electrode assemblies that utilize a metallization layer as described herein can reduce the amount of touch labor and time necessary to manufacture a shock wave catheter, which can also reduce the cost of such manufacturing and enable batch manufacturing of more electrode assemblies.

Figure 9:
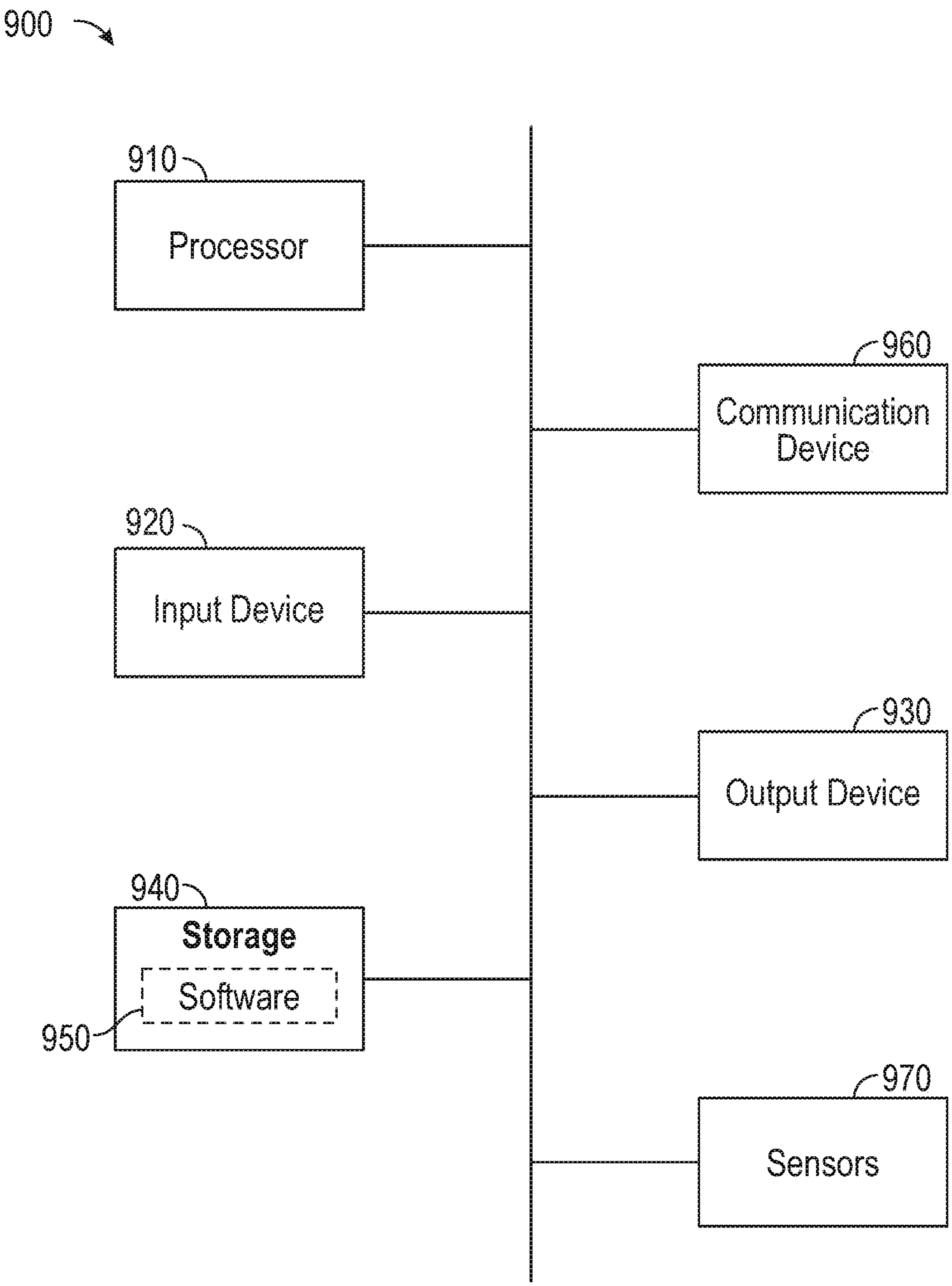
FIG. 9 illustrates an exemplary computing system, according to one or more aspects of the present disclosure.

FIG. 9 illustrates an example of a computing system 900 that may be part of, or used for controlling, a system comprising the catheters described herein. For example, system 900 may be used to control power source 28 of FIG. 1. System 900 may also be used to implement various methods of the present disclosure. System 900 can be a computer connected to a network, such as one or more networks of a hospital, including a local area network within a room of a medical facility and a network linking different portions of the medical facility, or a wide-area network accessed through the internet or other means. System 900 can be a client or a server. System 900 can be any suitable type of processor-based system, such as a personal computer, workstation, server, handheld computing device (portable electronic device), such as a phone or tablet, or dedicated device. System 900 can include, for example, one or more of input device 920, output device 930, one or more processors 910, storage 940, and communication device 960. Input device 920 and output device 930 can generally correspond to those described above and can either be connectable or integrated with the computer.

Input device 920 can be any suitable device that provides input, such as a touch screen, keyboard or keypad, mouse, gesture recognition component of a virtual/augmented reality system, or voice-recognition device. Output device 930 can be or include any suitable device that provides output, such as a display, touch screen, haptics device, virtual/augmented reality display, or speaker.

Storage 940 can be any suitable device that provides storage, such as an electrical, magnetic, or optical memory including a RAM, cache, hard drive, removable storage disk, or other non-transitory computer-readable medium. Communication device 960 can include any suitable device capable of transmitting and receiving signals over a network, such as a network interface chip or device. The components of the computing system 900 can be connected in any suitable manner, such as via a physical bus or wirelessly.

Processor(s) 910 can be any suitable processor or combination of processors, including any of, or any combination of, a central processing unit (CPU), field programmable gate array (FPGA), and application-specific integrated circuit (ASIC). Software 950, which can be stored in storage 940 and executed by one or more processors 910, can include, for example, the programming that embodies the functionality or portions of the functionality of the present disclosure (e.g., as embodied in the devices as described above).

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport computer-readable medium can include, but is not limited to, an electronic, magnetic, optical, electromagnetic, or infrared wired or wireless propagation medium.

System 900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 900 can implement any operating system suitable for operating on the network. Software 950 can be written in any suitable programming language, such as C, C++, Java, or Python. In various examples, application software embodying the functionality of the present disclosure can be deployed in different configurations, such as in a client/server arrangement or through a Web browser as a Web-based application or Web service.

In some examples, system 900 includes one or more sensors 970. One or more sensors 970 may be integrated with a catheter, such as catheter 10 of FIG. 1. One or more sensors 970 may be separate from a catheter, such as one or more sensors of a separate system. One or more sensors 970 may be positioned at any location on a catheter, such as catheter 10. For instance, with respect to catheter 10, the sensors 970 may be positioned proximal to one or more emitters 16, distal from one or more emitters 16, and/or intermediary between one or more emitters 16 (or any combination thereof), and one or more sensors 970 may be positioned within the flexible cap 18 or external to the flexible cap 18. One or more sensors 970 may be positioned within a patient (e.g., within the body lumen within which a catheter is positioned or within another region of the patient) or outside of a patient. For instance, certain sensors, such as a pressure sensor, may be positioned outside of an enclosure of the catheter, e.g., the flexible cap 18, and/or outside of the patient to measure pressure when components are in fluid communication. One or more sensors 970 may include one or more of any suitable sensor devices, such as a pressure sensor, a thermal sensor, an electrical sensor (e.g., current, voltage, resistance, and/or impedance sensors), or a visualization sensor (e.g., an optical imaging sensor, an ultrasonic imaging sensor, etc.). Sensors 970 can provide feedback to an operator using a catheter, such as catheter 10, by measuring parameters in the surrounding environment and thereby indicating a status of the catheter and components thereof, and further providing for guidance on what further steps the operator may decide to implement with the catheter. For example, in implementations where sensors 970 include pressure sensors, a slight decrease in pressure may indicate success at cracking a calcified lesion, due to the fact that the expandable member surrounding the emitters is able to further expand without changing the volume of fluid within the expandable member. Further, a significant decrease in pressure may indicate a rupture failure mode where the expandable member has lost seal and fluid volume, and thus guiding toward withdrawal of the device. In implementations where the sensors include a visualization sensor, an operator of the catheter may be able to more clearly understand where the catheter device is located relative to a target lesion or anatomy, prior to, during, and after delivering therapy.

Although the catheter devices described herein have been discussed primarily in the context of treating coronary occlusions, such as lesions in vasculature, the catheter devices described herein can be used for a variety of occlusions, such as occlusions in the peripheral vasculature (e.g., above-the-knee, below-the-knee, iliac, carotid, etc.). For further examples, various embodiments may be used for treating soft tissues, such as cancer and tumors (i.e., non-thermal ablation methods), blood clots, fibroids, cysts, organs, scar and fibrotic tissue removal, or other tissue destruction and removal treatments. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal, and destruction of tissue, or used in place of thermal treatments or cauterization for venous insufficiency and fallopian ligation (i.e., for permanent female contraception).

In one or more examples, the electrode assemblies and, catheters described herein could also be used for tissue engineering methods, for instance, for mechanical tissue decellularization to create a bioactive scaffold in which new cells (e.g., exogenous and endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It should be noted that the elements and features of the example catheters illustrated throughout this specification and drawings may be rearranged, recombined, and modified without departing from the present invention. For instance, while this specification and drawings describe and illustrate catheters having several example balloon designs, the present disclosure is intended to include catheters having a variety of balloon configurations. The number, placement, and spacing of the electrode pairs of the shock wave generators can be modified without departing from the subject invention. Further, the number, placement, and spacing of balloons of catheters can be modified without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A catheter comprising:
an elongate tube;
a flexible circuit, wrapped at least partially around the elongate tube, the flexible circuit including:
a flexible substrate;
a first trace formed on the flexible substrate and forming a first electrode; and
a first insulation layer overlaying the first trace and having at least one cutout that is aligned with the first electrode; and
a second electrode disposed radially outward from the first electrode relative to a longitudinal axis of the elongate tube, the first insulation layer separating the second electrode and the first electrode by a gap such that, when a voltage pulse is applied across the first electrode and the second electrode, current flows across the gap.

2. The catheter of claim 1, wherein the first trace is formed in a metallization layer of the flexible circuit.

3. The catheter of claim 1, wherein the second electrode includes at least one hole aligned with the at least one cutout in the first insulation layer to form the gap between the first electrode and the second electrode.

4. The catheter of claim 1, wherein the second electrode comprises a conductive band.

5. The catheter of claim 1, wherein the flexible circuit further comprises first and second conductive layers disposed on either side of a second insulation layer, the first conductive layer including the first trace.

6. The catheter of claim 1, wherein the flexible circuit comprises a second trace that forms the second electrode.

7. The catheter of claim 6, wherein the flexible circuit comprises a first leg extending in a longitudinal direction, a second leg circumferentially offset from the first leg, and a connecting portion connecting the first leg and the second leg, wherein the first leg comprises the first electrode and the second electrode.

8. The catheter of claim 7, wherein the first electrode and the second electrode form a first shock wave emitter and the second leg includes a second shock wave emitter.

9. The catheter of claim 8, wherein the flexible circuit comprises a third leg circumferentially offset from the first leg and the second leg, the third leg including a third shock wave emitter.

10. A system comprising:
a power source; and
a catheter comprising:
an elongate tube;
a flexible circuit, wrapped at least partially around the elongate tube, the flexible circuit including:
a flexible substrate;
a first trace formed on the flexible substrate and forming a first electrode; and
a first insulation layer overlaying the first trace and having at least one cutout that is aligned with the first electrode; and
a second electrode disposed radially outward from the first electrode relative to a longitudinal axis of the elongate tube, the first insulation layer separating the second electrode and the first electrode by a gap such that, when a voltage pulse is applied across the first electrode and the second electrode, current flows across the gap.

11. The system of claim 10, wherein the first trace is formed in a metallization layer of the flexible circuit.

12. The system of claim 10, wherein the second electrode includes at least one hole aligned with the at least one cutout in the first insulation layer to form the gap between the first electrode and the second electrode.

13. The system of claim 10, wherein the second electrode comprises a conductive band.

14. The system of claim 10, wherein the flexible circuit further comprises first and second conductive layers disposed on either side of a second insulation layer, the first conductive layer including the first trace.

15. The system of claim 10, wherein the flexible circuit comprises a second trace that forms the second electrode.

16. The system of claim 15, wherein the flexible circuit comprises a first leg extending in a longitudinal direction, a second leg circumferentially offset from the first leg, and a connecting portion connecting the first leg and the second leg, wherein the first leg comprises the first electrode and the second electrode.

17. The system of claim 16, wherein the first electrode and the second electrode form a first shock wave emitter and the second leg includes a second shock wave emitter.

18. The system of claim 17, wherein the flexible circuit comprises a third leg circumferentially offset from the first leg and the second leg, the third leg including a third shock wave emitter.

* * * * *